US006821521B1

(12) United States Patent
Robinson et al.

(10) Patent No.: US 6,821,521 B1
(45) Date of Patent: Nov. 23, 2004

(54) MULTICOMPONENT MENINGOCOCCAL VACCINE

(75) Inventors: Andrew Robinson, Salisbury (GB); Andrew Richard Gorringe, Salisbury (GB); Michael John Hudson, Salisbury (GB); Karen Margaret Reddin, Salisbury (GB)

(73) Assignee: Health Protection Agency, Salisbury (GB)

( * ) Notice: Subject to any disclaimer, the term of this patent is extended or adjusted under 35 U.S.C. 154(b) by 0 days.

(21) Appl. No.: 09/830,854

(22) PCT Filed: Nov. 2, 1999

(86) PCT No.: PCT/GB99/03626

§ 371 (c)(1),
(2), (4) Date: Aug. 29, 2001

(87) PCT Pub. No.: WO00/25811

PCT Pub. Date: May 11, 2000

(30) Foreign Application Priority Data

Nov. 2, 1998 (GB) .............................. 9823978

(51) Int. Cl.[7] ...................... A61K 39/095; A61K 39/00; C12P 21/04; C07K 1/00
(52) U.S. Cl. ............................... 424/249.1; 424/250.1; 424/184.1; 530/350; 435/69.7
(58) Field of Search .......................... 424/249.1, 250.1, 424/184.1; 530/350; 435/69.7

(56) References Cited

U.S. PATENT DOCUMENTS 6,180,111 B1    1/2001   Stein et al.

FOREIGN PATENT DOCUMENTS

| EP | 0 301 992 B1 | 5/1995 | .......... A61K/39/95 |
|----|--------------|--------|----------------------|
| EP | 0 560 968 B1 | 7/1996 | .......... A61K/39/95 |
| EP | 0 528 787 B1 | 12/1998 | .......... A61K/39/95 |
| WO | WO 90/06696 A3 | 6/1990 | .......... A31K/39/095 |
| WO | WO 90/06696 A2 | 6/1990 | .......... A31K/39/095 |
| WO | WO 90/12591 | 11/1990 | .......... A61K/39/095 |
| WO | WO 93/06861 | 4/1993 | .......... A61K/39/098 |
| WO | WO 94/08021 A1 | 4/1994 | .......... C12N/15/61 |
| WO | WO 98/56901 A2 | 12/1998 | .......... C12N/15/00 |
| WO | WO 01/09350 A2 | 2/2001 | .......... C12N/15/74 |

OTHER PUBLICATIONS

Gomez et al. "Effect of adjuvants in the isotypes and bacterial activity of antibodies against the transferrin–binding proteins of *Neisserria meningitidis*" Vaccine, vol. 16, No. 17 pp. 1633–1639, Oct. 1998.*
Dlawer et al. "The meningococcal transferrin–binding proteins 1 and 2 ... " Vaccine, vol. 14, No. 1 pp. 49–53, 1996.*
Dlawer et al. "Immune Responses in Humans and Animals to Meningococcal Transferrin–Binding Proteins: Implications for Vaccine Design" Infection and Immunity, vol. 62, No. 7, pp. 2984–2990, Jul. 1994.*

Ala'Aldeen, D.A.A., "Transferrin receptors of *Neisseria meningitidis*: promising candidates for a broadly cross–protective vaccine," *J. Med. Microbiol.* 44:237–243, The Pathological Society of Great Britain and Ireland (1996).
Boulton, I.C. et al., "Transferrin–binding protein B isolated from *Neisseria meningitidis* discriminates between apo and diferric human transferrin," *Biochem. J.* 334:269–273, London Portland Press On Behalf Of The Biochemical Society (1998).
Gómez, J.A. et al., "Effect of adjuvants in the isotypes and bactericidal activity of antibodies against the transferrin–binding proteins of *Neisseria meningitidis*," *Vaccine* 16:1633–1639, Elsevier (1998).
Gorringe, A.R. et al., "Human antibody response to meningococcal transferrin binding proteins: evidence for vaccine potential," *Vaccince* 13:1207–1212, Elsevier Science Ltd. (1995).
Tabatabai, L.B. et al., "Modulation of immune responses in Balb/c mice vaccinated with *Brucella abortus* Cu–Zn superoxide dismutase synthetic peptide vaccine," *Vaccine* 12:919–924, Butterworth–Heinemann Ltd. (1994).
Wilks, K.E. et al., "Periplasmic Superoxide Dismutase in Meningococcal Pathogenicity," *Infection and Immunity* 66:213–217, American Society for Microbiology (1998).
International Search Report of International Application No. PCT/GB 99/03626, Jun. 13, 2000.
Brandileone, M.C., et al., "Induction of Iron Regulated Proteins During Normal Growth of *Neisseria meningitidis* in a Chemically Defined Medium," *Rev. Inst. Med. Trop. São Paulo36*: 301–310, Instituto de Medicina Tropical de Sān Paulo (1994).
Legrain, M., et al., "Production of Lipidated Meningcocal Transferrin Binding Protein 2 in *Escherichia coli*," *Prot. Expr. Purif.* 6: 570–578, Academic Press Inc. (1995).
Lissolo, L., et al., "Evaluation of Transferrin–Binding Protein 2 within the Tranferrin–Binding Protein Complex as a Potential Antigen for Future Meningococcal Vaccines," *Infect. & Immun.* 63:884–890, American Society for Microbiology (1995).

(List continued on next page.)

*Primary Examiner*—Rodney P Swartz
*Assistant Examiner*—Khatol Shahnan Shah
(74) *Attorney, Agent, or Firm*—Sterne, Kessler, Goldstein & Fox PLLC (57) ABSTRACT

A composition comprising Transferrin binding proteins A and B is described (TbpA and TbpB). The composition is suitable for use in vaccines and for treatment of Gram negative bacterial infection, particularly meningococcal infection, demonstrating a broad spectrum of protection to a number of different bacterial pathogens. Also described are compositions comprising Tbps and other components, such as neisserial outer membrane vesicles and Cu,Zn-Superoxide dismutase. Methods for preparation of these compositions and their uses in vaccination against disease are further provided.

8 Claims, 9 Drawing Sheets-

OTHER PUBLICATIONS

Oftung, F., et al., "A mouse model utilising human transferrin to study protection against *Neisseria meningitidis* serogroup B induced by outer membrane vesicle vaccination," *FEMS Immunol. Med. Microbiol.* 26:75–82, Elsevier Science B.V. (Oct. 1999).

Pintor, M., et al. "Blocking of iron uptake from transferrin by antibodies against the transferrin binding proteins in *Neisseria meningitidis*," *Mircrobial Pathogen.* 20:127–139, Academic Press Ltd. (1996).

Rokbi, B., et al., "Evaluation of Recombinant Tranferrin-Binding Protein B Variants from *Neisseria meningitidis* for Their Ability to Induce Cross–Reactive and Bactericidal Antibodies against a Genetically Diverse Collection of Serogroup B Strains," *Infect. Immun.* 65:55–63, American Society for Microbiology. (Jan. 1997).

Schryvers, A.B. and Stojiljkovic, I., "MicroReview. Iron acquisition systems in the pathogenic *Neisseria,*" *Molec. Microbiol.* 32:1117–1123, Blackwell Science Ltd. (Jun. 1999).

Van der Ley, P. and Poolman, J.T., "Construction of a Multivalent Meningococcal Vaccine Strain Based on the Class 1 Outer Membrane Protein," *Infect. & Immun.* 60:3158–3161, American Society for Microbiology (1992).

Van der Ley, P., et al., "Use of Transformation To Construct Antigenic Hybrids of the Class 1 Outer Membrane Protein in *Neisseria meningitidis,*" *Infect. & Immun.* 61:4217–4224, American Society for Microbiology (1993).

Van der Ley, P., et al., "Construction of *Neisseria meningitidis* strains carrying multiple chromosomal copies of the *porA* gene for use in the production of a multivalent outer membrane vesicle vaccine," *Vaccine* 13:401–407, Elsevier Science Ltd. (1995).

Van der Voort, E.R. et al., "Specificity of Human Bactericidal Antibodies against PorA P1.7,16 Induced with a Hexavalent Meningococcal Outer Membrane Vesicle Vaccine," *Infect. & Immun.* 64:2745–2751, American Society for Microbiology (1996).

Van der Voort, E.R., et al., "Human B–and T–Cell Responses after Immunization with a Hexavalent PorA Meningococcal Outer Membrane Vesicle Vaccine," *Infect. & Immun.* 65:5184–5190, American Society for Microbiology (Dec. 1997).

English language translation of European Patent No. EP 0 560 968 (Document AM2), Frank B. Dehn & Co., London, UK (1996).

Dialog File 351, Accession No. 9748403, Derwent WPI English language abstract for EP 0 586 266 A1 (Document AP1).

Copy of Notice of Opposition for European Patent No. 1 126 874 (Mar. 2004).

Claassen, I., et al., "Production, characterization and control of a *Neisseria meningitidis* hexavalent class 1 outer membrane protein containing vesicle vaccine," *Vaccine* 14:1001–1008, Elsevier Science, Ltd. (1996).

Peeteers, C.C.A.M., et al., "Phase I clinical trial with a hexavalent PorA containing meningococcal outer membrane vesicle vaccine," *Vaccine* 14:1009–1015, Elsevier Science, Ltd. (1996).

* cited by examiner

MULTICOMPONENT MENINGOCOCCAL VACCINE

The present invention relates to a multicomponent vaccine and methods for preparing a multicomponent vaccine that confers protective immunity to a broad spectrum of infection by Gram negative pathogens. In particular the present invention relates to a multicomponent vaccine that provides both passive and active protective immunity to meningococcal disease.

Meningococcal meningitis is a major problem worldwide and in many countries incidence of infection is increasing. *Neisseria meningitidis* is the causative agent of the disease and is also responsible for meningococcal septicaemia, which is associated with rapid onset and high mortality, with around 22% of cases proving fatal.

At present, vaccines directed at providing protective immunity against meningococcal disease provide only limited protection because of the many different strains of *N. meningitidis*. Vaccines based upon the serogroup antigens, the capsular polysaccharides, offer only short lived protection against infection and do not protect against many strains commonly found in North America and Europe. A further drawback of these vaccines is that they provide low levels of protection for children under the age of 2 years, one of the most vulnerable groups that are commonly susceptible to infection.

The meningococcal transferrin receptor is made up of two types of component protein chain, Transferrin binding protein A (TbpA) and TbpB. The receptor complex is believed to be formed from a dimer of TbpA which associates with a single TbpB (Boulton et al. (1998)). Epitopes present in TbpA are known to be masked within the interior of the protein (Ala'Aldeen (1996)). Vaccines against meningococcal meningitis based on TbpB from one strain alone show some cross reactivity and there is evidence of a cross-reactive immune response in rabbits immunised with TbpB alone (Feirrerós et al. (1998)).

Gomez et al (Vaccine Vol. 16 (1998) No. 17 pp. 1633–1633) describes a study on the effects of a number of different adjuvant compositions in vaccines comprising TbpA+TbpB complex. Immunization rates against meningococcal challenge were highest in compositions comprising TbpA+TbpB and RAS adjuvant.

Ala'Aldeen (J. Med. Microbiol. Vol. 44 (1996) pp. 237–237 provides a review of Tbps of *N. meningitidis* and their potential use as candidate vaccine antigens. Ala'Aldeen suggests that cross reactivity and broad spectrum protection is mainly associated with the TbpB subunit (page 240, third paragraph).

Gorringe et al (Vaccine Vol. 13 (1995) No. 13 pp. 1207–1207) describes the human antibody response to Tbps and evaluates their value as vaccine antigens by testing human sera for anti-Tbp antibodies. Gorringe et al does not describe the components of any such vaccine, but investigates the levels of antibody cross reactivity between purified TbpA and TbpB subunits and TbpA+B complex.

Boulton et al (Biochem. J. (1998) 334 pp. 269–273) describes the isolation and characterisation of TbpB from *N. meningitidis* and also postulates the make-up of the Tbp complex in vivo as a TbpA dimer plus TbpB monomer.

It would be of advantage, nevertheless, to provide a vaccine that gives a broader range of protective immunity to infection from a wider spectrum of strains of *N. meningitidis*. It would be of further advantage to provide a vaccine that confers protective immunity to infants as well as adults and whose protection is long term. It would also be of advantage to provide a vaccine that protects against sub-clinical infection, i.e. where symptoms of meningococcal infection are not immediately apparent that the infected individual may act as a carrier of the pathogen.

It is an object of the present invention to provide compositions containing Tbps, and vaccines based thereon, that meet or at least ameliorate the disadvantages in the art. In particular, it is an object of the invention to provide a vaccine composition that consistently and reliably induces protective immunity to meningococcal infection.

Accordingly, a first aspect of the present invention provides a composition comprising both transferrin binding proteins A (TbpA) and B (TbpB), suitably in a molar ratio of about 2:1 (TbpA:TbpB). In a preferred embodiment of the present invention the molar ratio of TbpA to TbpB is 2:1.

The composition may be combined with a pharmaceutically acceptable carrier—for example the adjuvant alum although any carrier suitable for oral, intravenous, subcutaneous, intraperitoneal or any other route of administration is suitable—to produce a pharmaceutical composition for treatment of meningococcal disease.

The present invention thus provides for a vaccine comprising both TbpA+B proteins, preferably with a molar ratio of between 1.8 and 2.2 molecules of TbpA to one molecule of TbpB, more preferably 2 molecules of TbpA to one of TbpB. This particular combination of components, surprisingly, can provide higher protective immunity to meningococcal infection, compared to vaccination with TbpB alone. In a specific embodiment of the invention, described in more detail below, a 1:1 combination of A:B is more protective against challenge than B alone. This is surprising as TbpA has previously been considered to be non-protective. The present results differ from this established view with some experiments (described in more detail below) showing that, when administered as a vaccine, TbpA is also able to provide protective immunity to meningococcal infection. However, the present results most strikingly demonstrate the consistent performance of vaccines that comprise both Tbps A and B compared to those comprising Tbp A or B alone. It is this lack of variability between compositions and the consistently high level of protection to infection induced in response to vaccination with Tbp A+B, that enables the compositions of the invention to demonstrate significant advantage over the vaccines of the prior art.

Transferrin binding proteins are known to be located on the outer membranes of a number of Gram negative bacteria such as *N. meningitidis*. Formulations of the composition of the present invention with conventional carriers or adjuvants provide a composition for treatment of infection by these bacteria.

It is an advantage that following administration of a composition according to the present invention antibodies may be raised against epitopes that consist of sequences from TbpA and TbpB in juxtaposition. Thus, the immune response obtainable using such a composition may be improved compared with that from prior art vaccine compositions which comprise only one component of the Tbp complex and in which the full range of potential Tbp epitopes are unavailable. It is a further option in the present invention for one Tbp subunit component of the TbpA+B complex to be from a first strain of *N. meningitidis* and another from a second strain different from the first. For example, the TbpA dimer is taken from the first strain and the TbpB is from the second. The TbpA and TbpB proteins may be selected independently from strains K454, H44/76 and B16B6. In all aspects of the invention the Tbps can be directly isolated from the bacterial source or can be produced by recombinant methods commonly known in the art. Combinations of proteins from other strains are also envisaged, and the combining of components from different strains of bacteria offers the potential for providing an individual with a broader spectrum of protection against meningococcal infection. It is further optional for a composition or vaccine of the invention to contain a mixture of A proteins from different strains or a mixture of B proteins from different strains, broadening further the potential spectrum of protection conferred by the invention. A still further option is for Tbps to be obtained from or derived from other bacteria, including *N. gonorrhoeae, N. lactamica* and *Moraxella catarrhalis*.

In the present invention, the term "transferrin binding protein" or "Tbp" refers to a protein which either alone binds to transferrin or can be part of a complex of proteins that binds transferrin. The term also embraces fragments, variants and derivatives of such a protein provided that antibodies raised against the fragment, variant or derivative bind the protein. Thus, TbpA and TbpB either dissociated or associated into a complex are considered to be Tbp. Moreover, mutants, fusion proteins or fragments of either TbpA or B or other derivatives of the TbpA+B complex with a common antigenic identity are also considered to be represented by the term Tbp in the present invention.

A second aspect of the invention provides a composition comprising a complex of two TbpAs and one TbpB. The proteins are thus held together in the ratio seen in the native receptor. The individual proteins may be linked, for example, by hydrogen bonds or covalent bonds. In the latter case, each TbpA is covalently linked to the TbpA, either directly or indirectly. In a preferred embodiment, the complex of TbpA and TbpB assumes a native configuration.

A native TbpA+B complex may be isolated and purified from *N. meningitidis*. Alternatively, the invention also provides for synthesis of recombinant Tbp protein followed by assembly of the TbpA+B complex in vitro. The TbpA+B complex may be formed by admixture, or may be crosslinked by physical (e.g. UV radiation) or chemical methods known to the art, resulting in a combination of Tbps that will remain together and can not dissociate from each other. In a further example, a single chain recombinant protein comprising two TbpA sequences, preferably in the form of the TbpA dimer, is then covalently linked with TbpB protein to form a complete TbpA+B complex in vitro. Another example of the invention in use provides that TbpA and B are mutated so as to introduce cysteine residues that facilitate the formation of disuiphide bridges between the TbpA and TbpB subunits, so as to obtain a covalently bound complex.

In preparation of a recombinant protein TbpA and TbpB genes may also be truncated so that only those domains known to contribute to the antigenicity of the protein are incorporated in the Tbp complex.

In some compositions of the invention the TbpA+B complex is able to act as a transferrin receptor and binds to human transferrin. In other compositions of the invention the TbpA+B complex is non-functional in the sense that it does not bind transferrin, but it nevertheless provides an antigenic component that elicits an appropriate immune response.

A third aspect of the invention provides for a composition comprising a Tbp and *N. meningitidis* outer membrane vesicles. An advantage of this composition is that when administered to a vaccinee or patient it presents a different combination of *N. meningitidis* antigens, and particularly antigens that are in a formation substantially as present on the membrane of live infecting organisms. The combination offers the potential for a more effective protection against infection or a broader spectrum of protection than existing vaccines. Known methods of outer membrane vesicle isolation, such as by desoxycholate treatment, are suitable for preparation of compositions of the invention. In various preferred embodiments the Tbp is Tbp A, Tbp B or TbpA+B either in a native complex or in dissociated form.

The outer membrane vesicles may further be pretreated in vitro with Tbp so as to enrich the vesicle membrane with Tbp. By "enrich" and like terms, we refer to an outer membrane vesicle to which has been added Tbps so as to increase the concentration or density of Tbps in that vesicle. Preferably, the enrichment results in an outer membrane vesicle having an increased number of transferrin receptors located in the membrane, due to an increased concentration of TbpA and TbpB following their addition to the vesicle and their association into receptors or receptor-like structures. A particular advantage of such embodiments of the invention is that the Tbps, regarded as key antigenic components of the vaccine, are presented in a highly antigenic environment that closely mimics the environment in which transferrin receptors are presented on live, infecting bacteria.

As mentioned previously, the Tbp components of the composition need not be wild-type Tbps. They can be made recombinantly, and in so doing sequence alterations may be introduced. In one typical example of the invention, recombinant TbpB is modified so as to comprise a membrane binding domain. A preferred membrane spanning domain is a hydrophobic alpha helical region added to either the N or C terminus of the Tbp B protein. However, a membrane anchoring region need not only be an alpha helix, addition of a fatty acid or lipid chain would also facilitate membrane anchoring. In fact, wild type TbpB is believed to anchored to the bacterial outer membrane via such a lipid chain anchor. In a further example of the invention in use, the outer membrane vesicles are pretreated in vitro with membrane binding recombinant TbpB so as to enrich the vesicle membrane with TbpB. OMVs enriched with Tbps are additionally generated by inducing high levels of Tbp expression in *N. meningitidis* and then isolating OMVs via one of the methods described previously. This latter method is typically achieved by transforming the *N. meningitidis* host with a suitable expression vector into which has been inserted a gene or genes encoding the Tbps of choice. Suitable expression vectors for use in neisserial species include the plasmid pMGC10 (Nassif et al. (1991)).

It is preferred that the composition of the present invention comprises outer membrane vesicles and TbpA+B complexes isolated from a range of different strains of *N. meningitidis*. Other preferred compositions of the invention comprise other *N. meningitidis* proteins including surface antigens, periplasmic proteins, superoxide dismutase and glycoproteins.

The composition of the third aspect of the invention may instead of or in addition to outer membrane vesicles comprise one or more liposomes, each liposome including TbpA and/or TbpB preferably including TbpA and TbpB associated into a receptor or into a receptor-like complex. Thus a further means of presenting the transferrin receptor antigens is provided.

In a further embodiment of the third aspect of the invention, the composition comprises 22 kD antigen (Neisserial surface protein A (NspA)) as well as or instead of outer membrane vesicles. NspA and its preparation are described by Martin et al, 1997.

A fourth aspect of the invention provides for a vaccine comprising a composition of the invention as described above. A vaccine of the invention may also comprise antibodies to Tbp and thus provide a level of passive immunity to bacterial infection.

A fifth aspect of the invention provides for a method of manufacturing a composition that comprises combining TbpA, TbpB and N. meningitidis outer membrane vesicles with a pharmaceutically acceptable carrier. It is preferred that the molar ratio of TbpA to TbpB is about 2:1. The outer membrane vesicles can be pretreated in vitro with native TbpA+B so as to enrich the vesicle membrane with Tbp complex. However, the outer membrane vesicles may also be pretreated with other protein components so as to enrich them for these antigenic components also. The outer membrane vesicles may also be pretreated with antigenic proteins and proteoglycans from several different strains of N. meningitidis.

A further aspect of the invention provides for a composition comprising a Tbp and a Cu,Zn-Superoxide dismutase (Cu,Zn-SOD).

Figure 1:
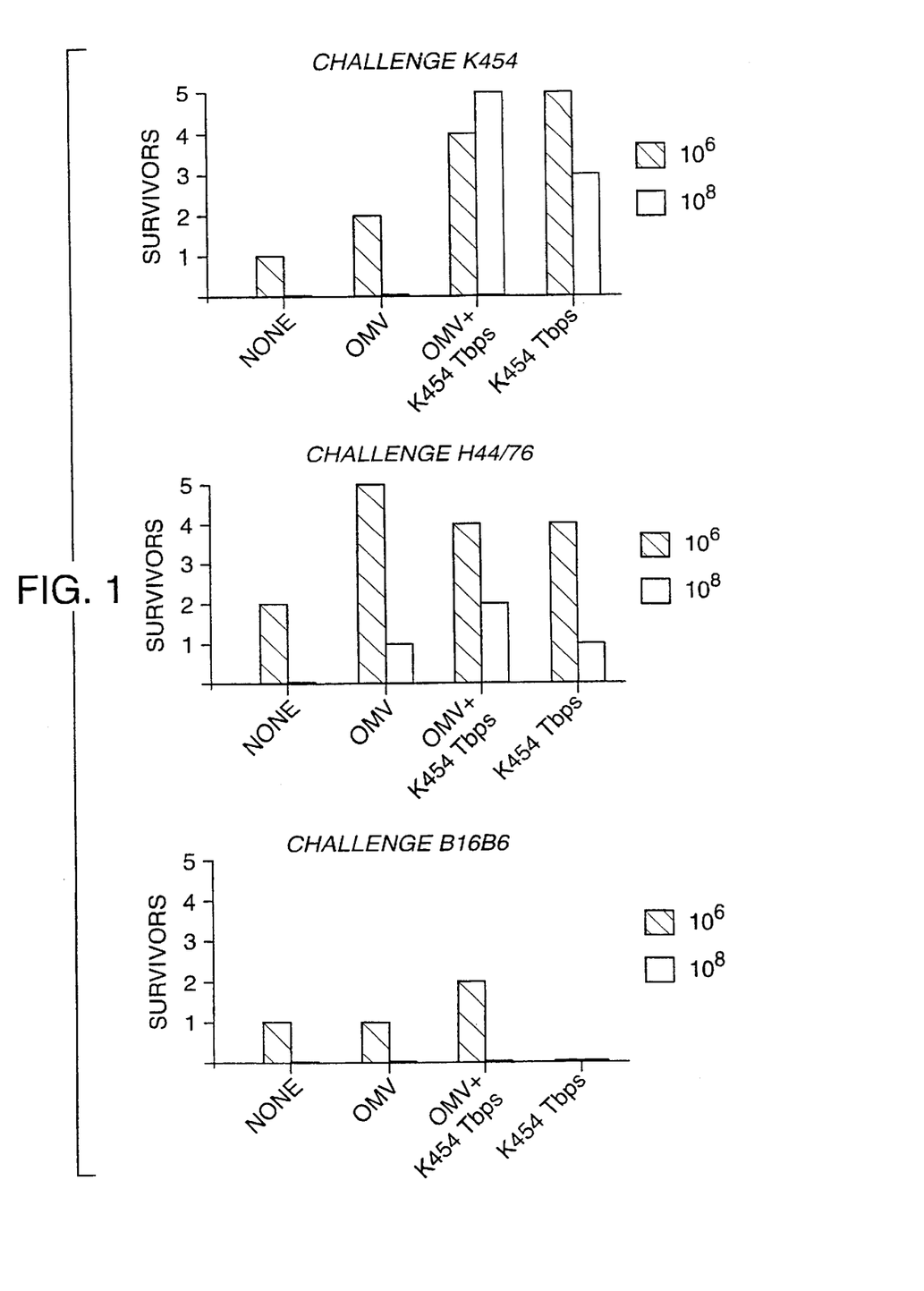
Figure 2:
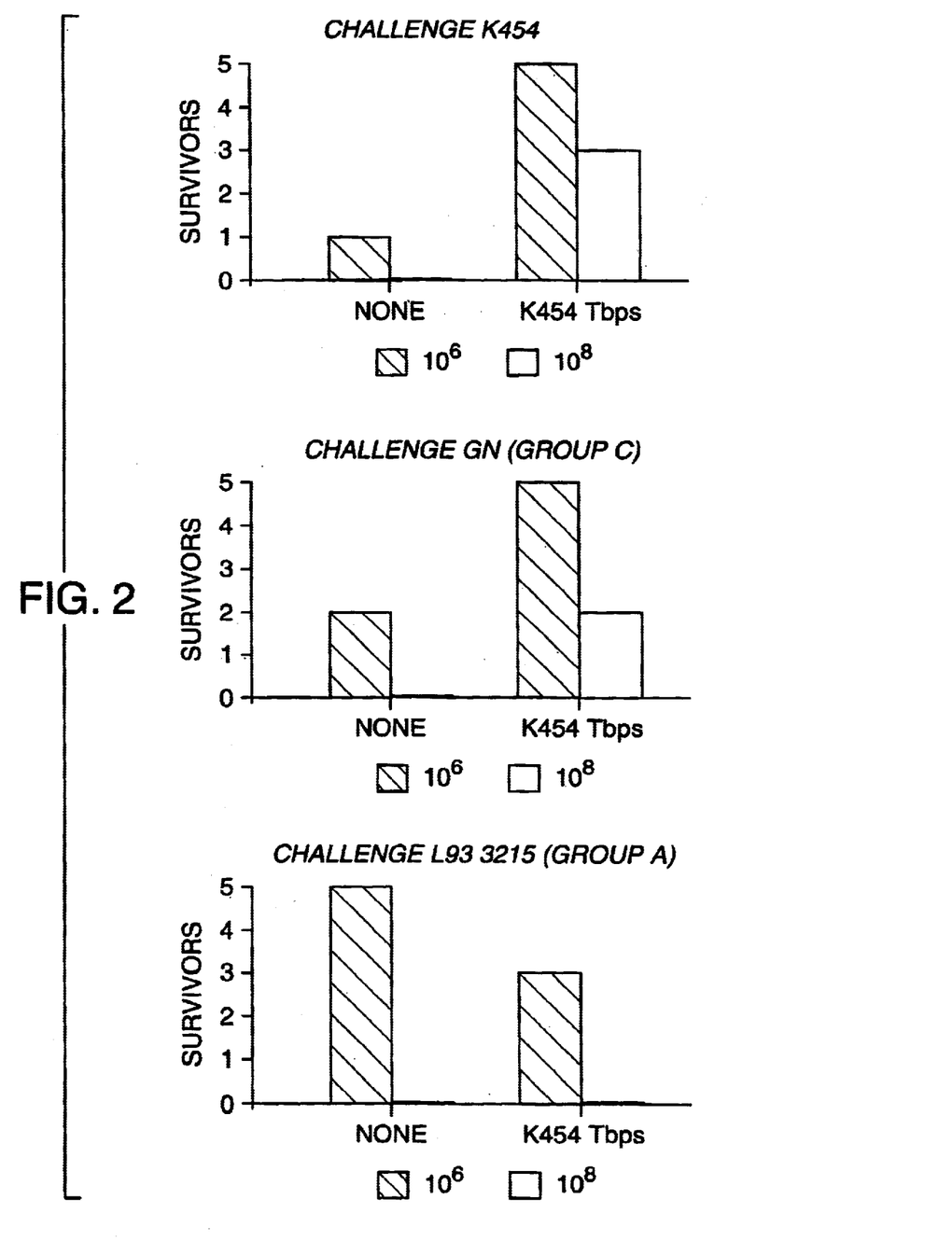
Figure 3:
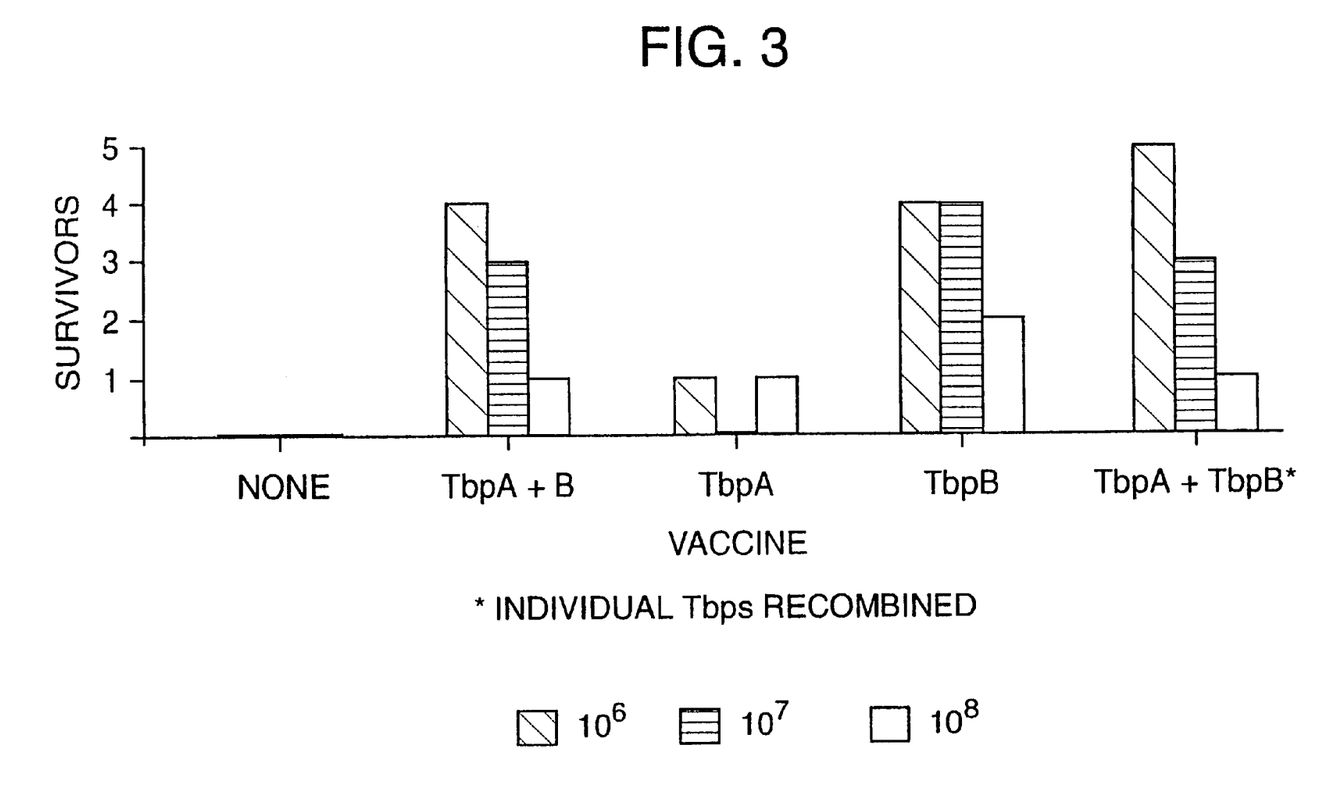
Figure 4A:
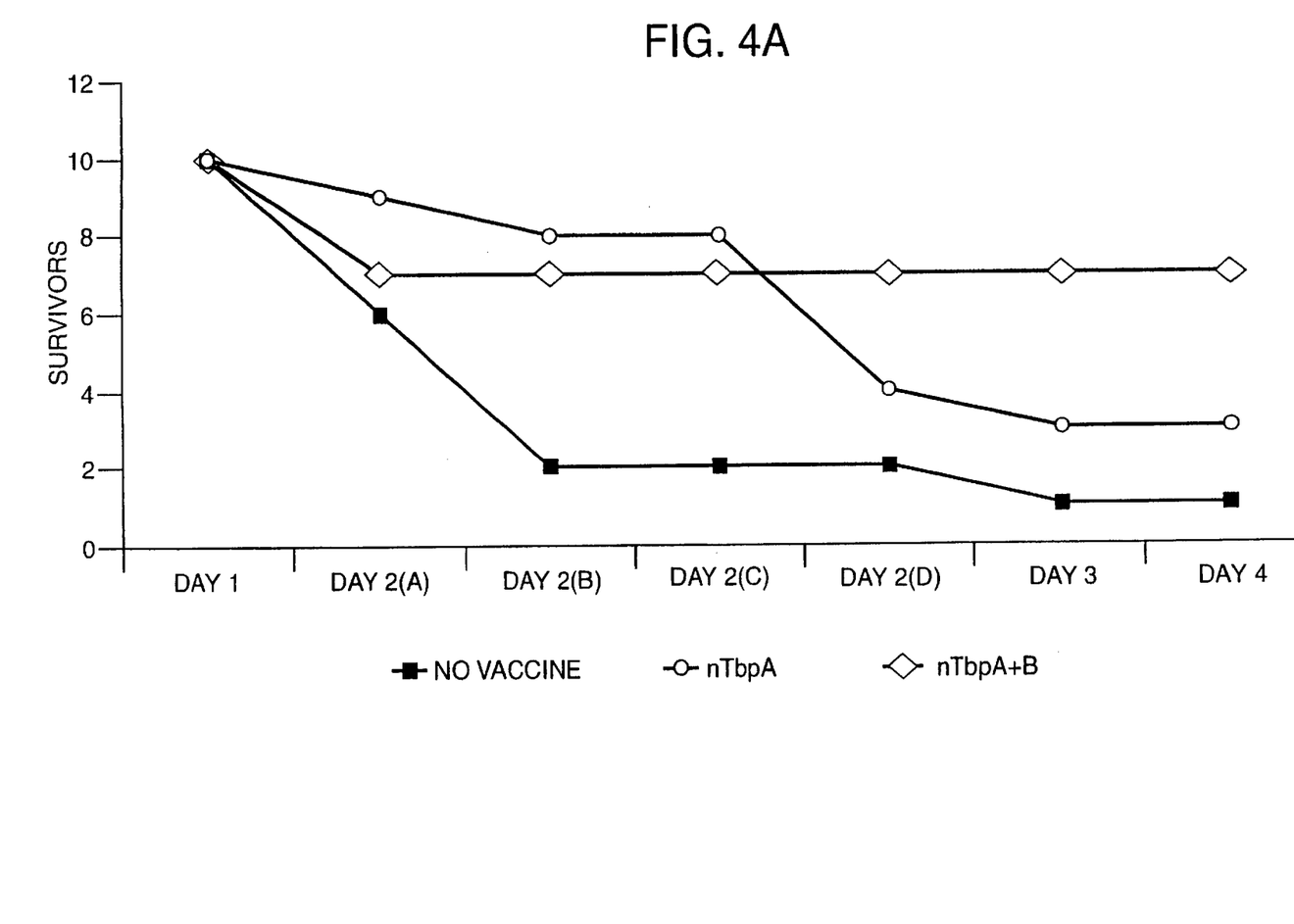
Figure 4B:
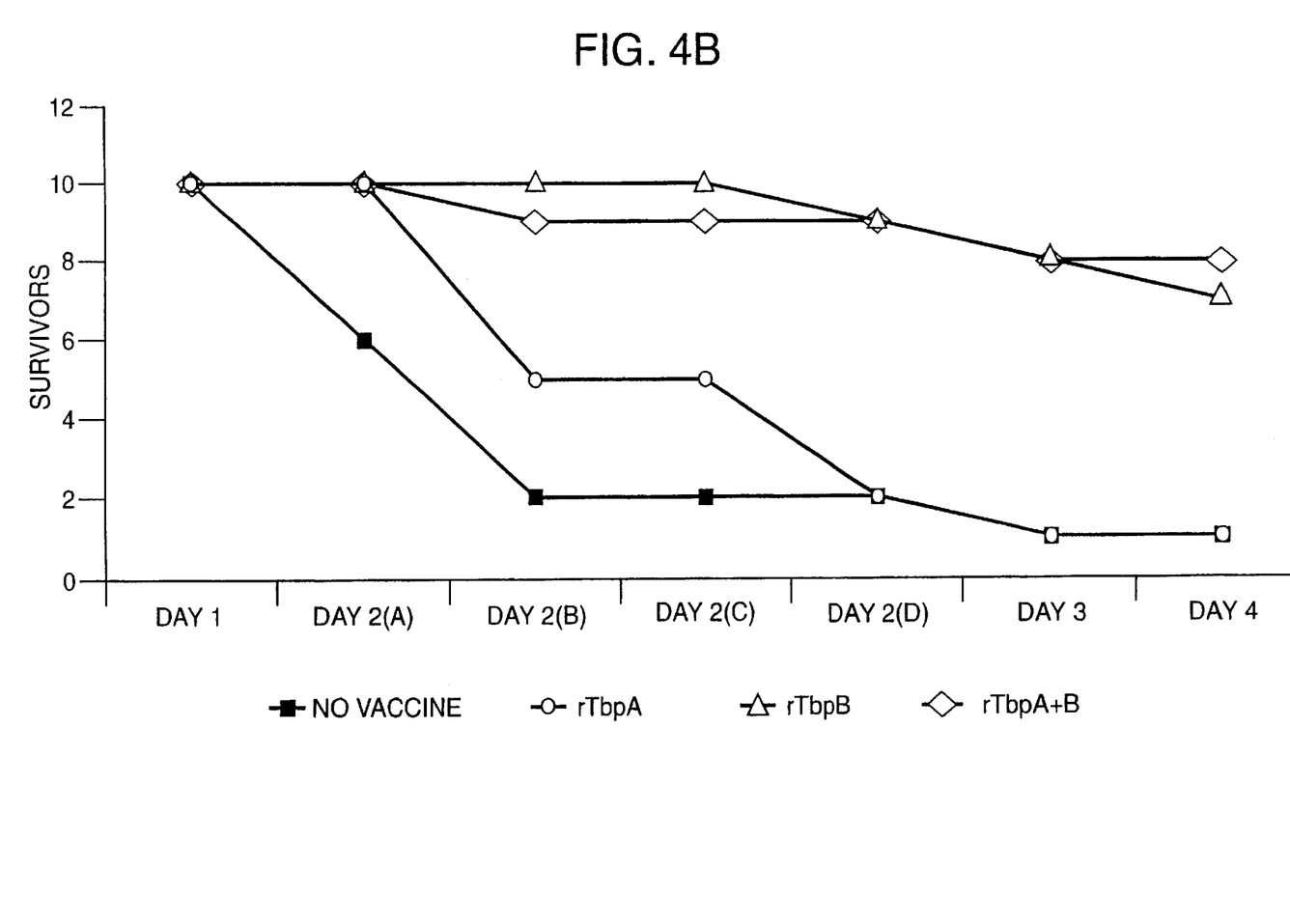

Cu,Zn-Superoxide Dismutase (Cu,Zn-SOD) is an metalloenzyme found in many prokaryotic and eukaryotic organisms. It catalyses the reduction of the superoxide radical anion, $O_2^-$, to hydrogen peroxide and molecular oxygen, thus playing an important role in the removal of cytotoxic free radicals from the organism. In bacteria Cu,Zn-SODs have been identified in the periplasm of a number of Gram negative species including *N. meningitidis*. The enzyme can exist as a dimer or a monomer, and accordingly in a preferred embodiment the present invention provides for a composition comprising a Tbp and a Cu,Zn-SOD of the dimeric type. As mentioned previously with regard to the use of the term "Tbp", the Cu,Zn-SOD of the present invention is also considered to encompass fragments, variants and derivatives of such a protein provided that antibodies raised against the fragment, variant or derivative bind the wild type Cu,Zn-SOD.

In examples of the invention in use, compositions are provided that comprise a Cu,Zn-SOD and either a TbpA, a TbpB or a TbpA+B complex. In the latter example it is preferred that the molar ratio of TbpA to Tbp B is between 1.8 and 2.2, with the most suitable compositions having a ratio of 2:1 (TbpA:TbpB). In further compositions of the invention the Tbps are from a different strain of *N. meningitidis* to that of the Cu,Zn-SOD, thus facilitating the formation of a broader spectrum of immune response to meningococcal infection.

The invention also provides for compositions wherein the Tbps and Cu,Zn-SOD are from different bacterial species, typically different Gram negative species. Such compositions thereby allow an even broader spectrum of immune response to be elicited when administered as a vaccine. Typical compositions comprise a neisserial TbpA+B complex as well as a monomeric Cu,Zn-SOD—from *E. coli* for example—and optionally a further dimeric Cu,Zn-SOD—for example from *Haemophilus parainfluenzae.*

Other aspects of the invention provide for methods of manufacturing compositions that provide protective immunity to Gram negative bacterial infection, comprising combining a covalently linked complex of TbpA and TbpB with either or both of *N. meningitidis* outer membrane vesicles and a Cu,Zn-SOD, plus a pharmaceutically acceptable carrier.

A still further aspect of the invention provides for a composition comprising Tbps and outer membrane vesicles, wherein the outer membrane vesicles are from different strains of *N. meningitidis*. By analogy, the invention also provides for compositions comprising Tbps and a Cu,Zn-SOD, wherein the Tbps are from different strains of *N. meningitidis.*

A further aspect provides for use of Tbps A and B in the manufacture of a medicament for human vaccination. It is preferred that such a medicament is suitable for vaccination against meningococcal infection, although some compositions of the invention provide broad spectrum protection to infection from a wider range of bacterial pathogens.

The embodiments of the invention are discussed in more detail by means of the Example described below. The results referred to in the Example are illustrated by the accompanying drawings, in which:

FIG. 1 shows immunisation of mice with TbpA+B and outer membrane vesicles;

FIG. 2 shows immunisation of mice with TbpA+B;

FIG. 3 shows protection of mice against IP infection after immunisation with TbpA+B, isolated TbpA or isolated TbpB;

FIGS. 4A and 4B show protection of mice against meningococcal infection following immunisation with either neisserial TbpA+B, TbpB or TbpA (nTbps) or recombinant Tbps (rTbps);

FIGS. 5A and 5B show protection of mice against challenges of $10^6$ and $10^7$ organisms/mouse of *N. meningitidis* strain K454 respectively, following immunisation with recombinant TbpA+B, TbpB or TbpA;

FIG. 6 shows protection against challenge with heterologous serogroup; and

FIG. 7 shows protection against challenge with B16B6

EXAMPLE

Mouse Protective Data

Mice (CAMR-NIH) were immunised with Tbps and/or outer membrane vesicles and challenged with either the homologous or a heterologous meningococcal strain. Survivors per group of mice immunised with Tbps from strain K454 and the outer membrane vesicle vaccine following challenge by strain K454 are shown in FIG. 1. Compared to Tbps, the outer membrane vesicle vaccine gave reduced protection but this may be because it is produced from a different group B strain (H44/76). Animals immunised with TbpA+B isolated from strain K454 were also protected against challenge with other serogroup B organisms (FIG. 1), with greater protection seen with the homologous strain and strains expressing a TbpB with a similar molecular weight. Little or no protection was observed against challenge with meningococci possessing TbpB with a very different molecular weight (strain B16B6). With the heterologous challenge strains, there is a slightly greater number survivors in the groups vaccinated with the combination of Tbps+outer membrane vesicles. However, the numbers involved are small and no definite conclusions can be reached. It is interesting to observe that mice immunised with TbpA+B from strain K454 were also protected against infection with a serogroup C but not a serogroup A strain (FIG. 2).

Protection against challenge-with strain K454 with mice immunised with co-purified TbpA+B and isolated TbpA and TbpB is shown in FIG. 3. It can be seen that TbpB is the predominant antigen responsible for protection, with little protection afforded by TbpA alone.

Recombinant TbpA and TbpB

TbpA and TbpB from *N. meningitidis* strain K454 were cloned and overexpressed in *E. coli*. The proteins were purified using affinity chromatography and used to determine their protective potency in a mouse model of meningococcal disease. Recombinant Tbps showed equivalent protection to that provided by Tbps isolated from iron-stressed *N. meningitidis* (FIGS. 4A and 4B). These recombinant Tbps were also utilised in two further larger IP challenge experiments (FIGS. 5A–B).

The strong and consistent protective potency of Tbps against mouse I.P. infection with *N. meningitidis* is probably the most compelling evidence for their vaccine potential.

Figure 5A:
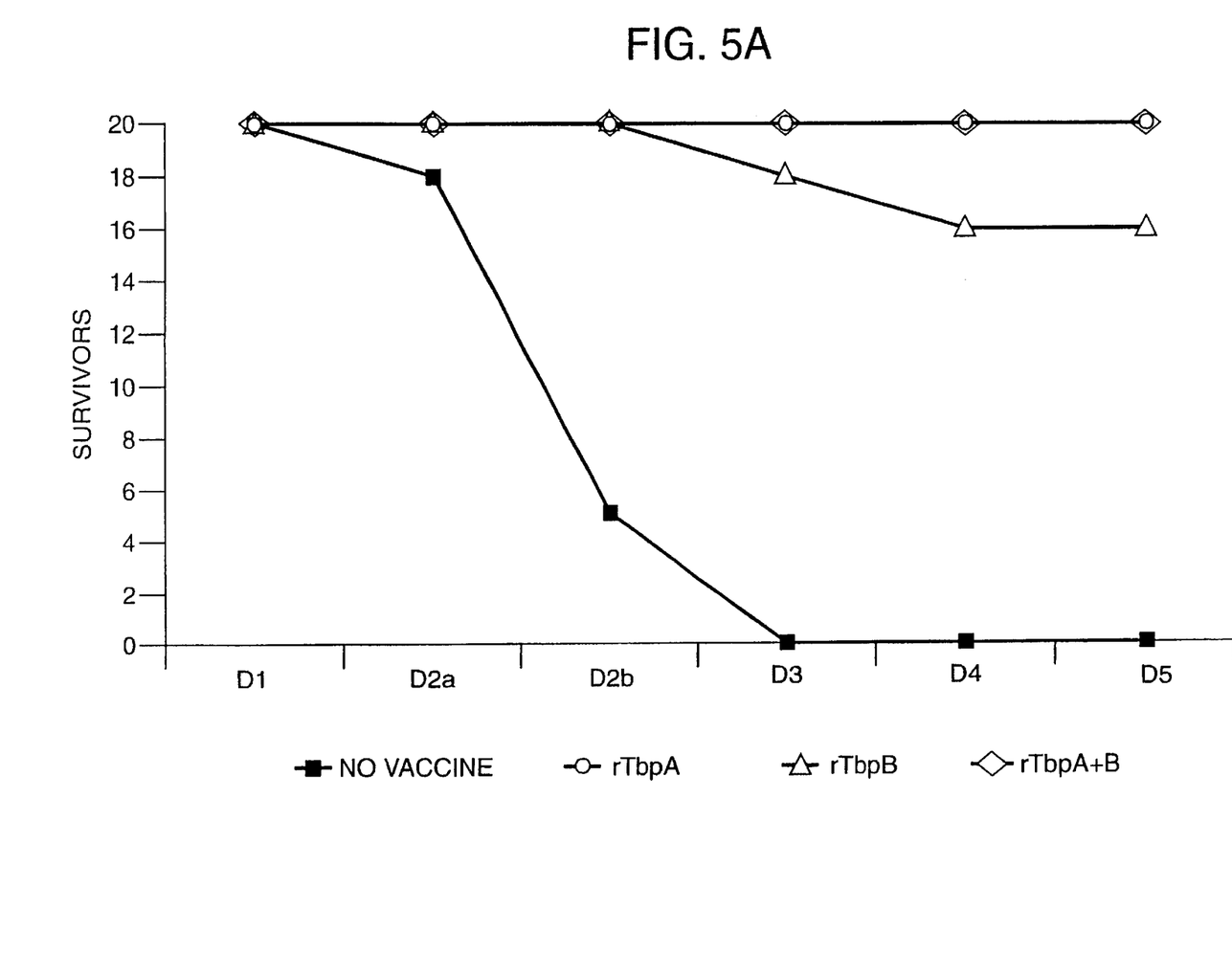
Figure 5B:
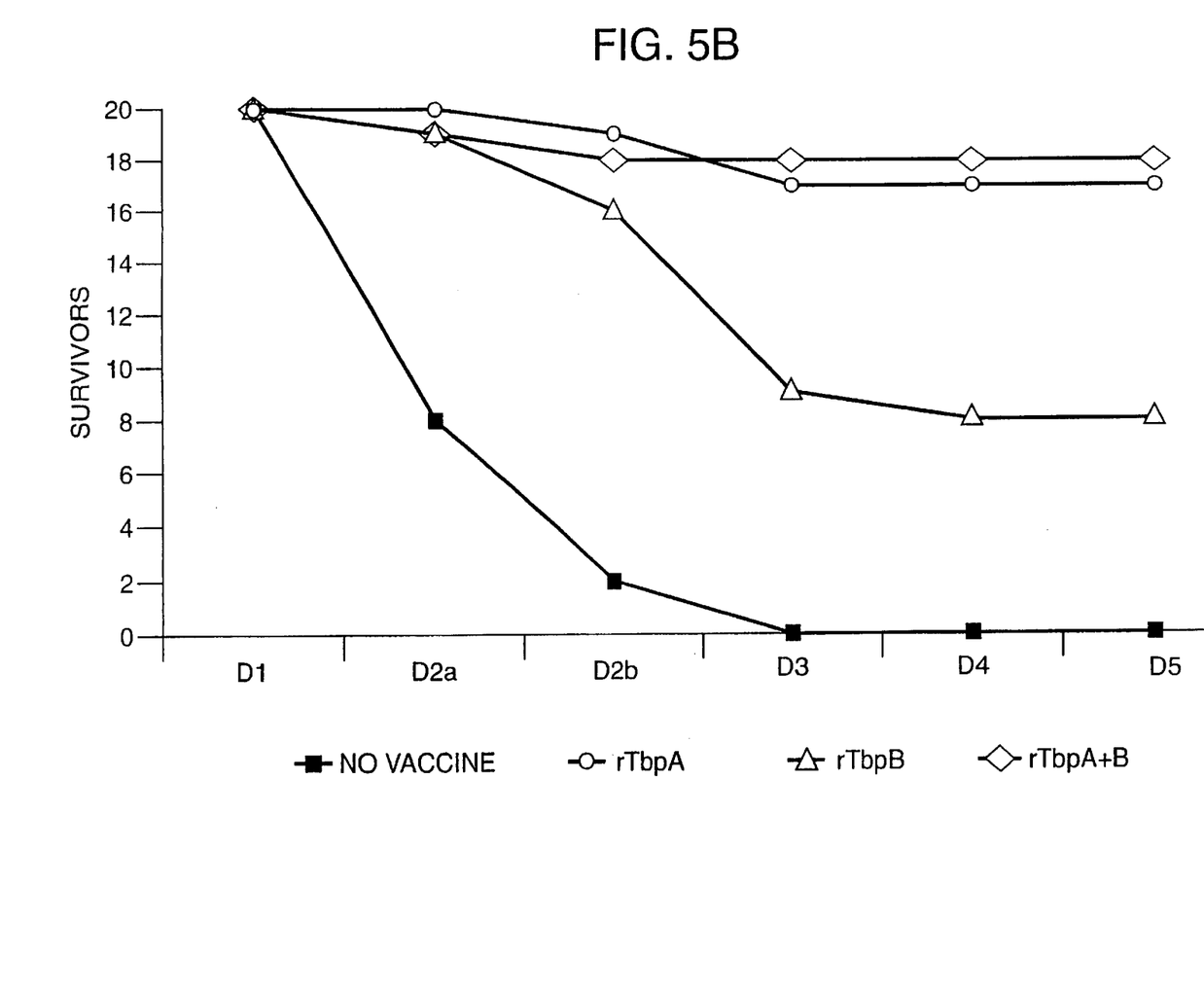
Figure 6:
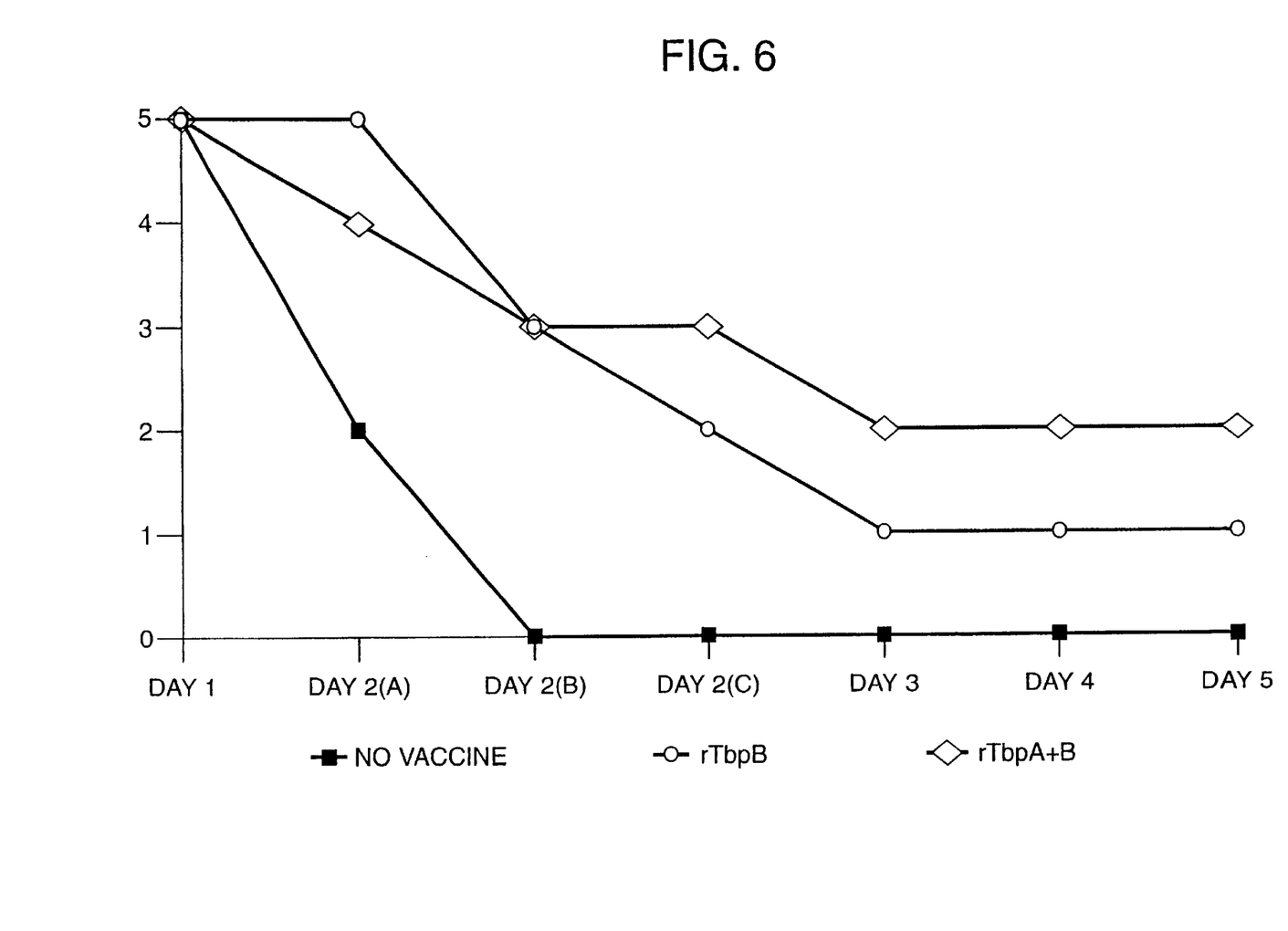
Figure 7:
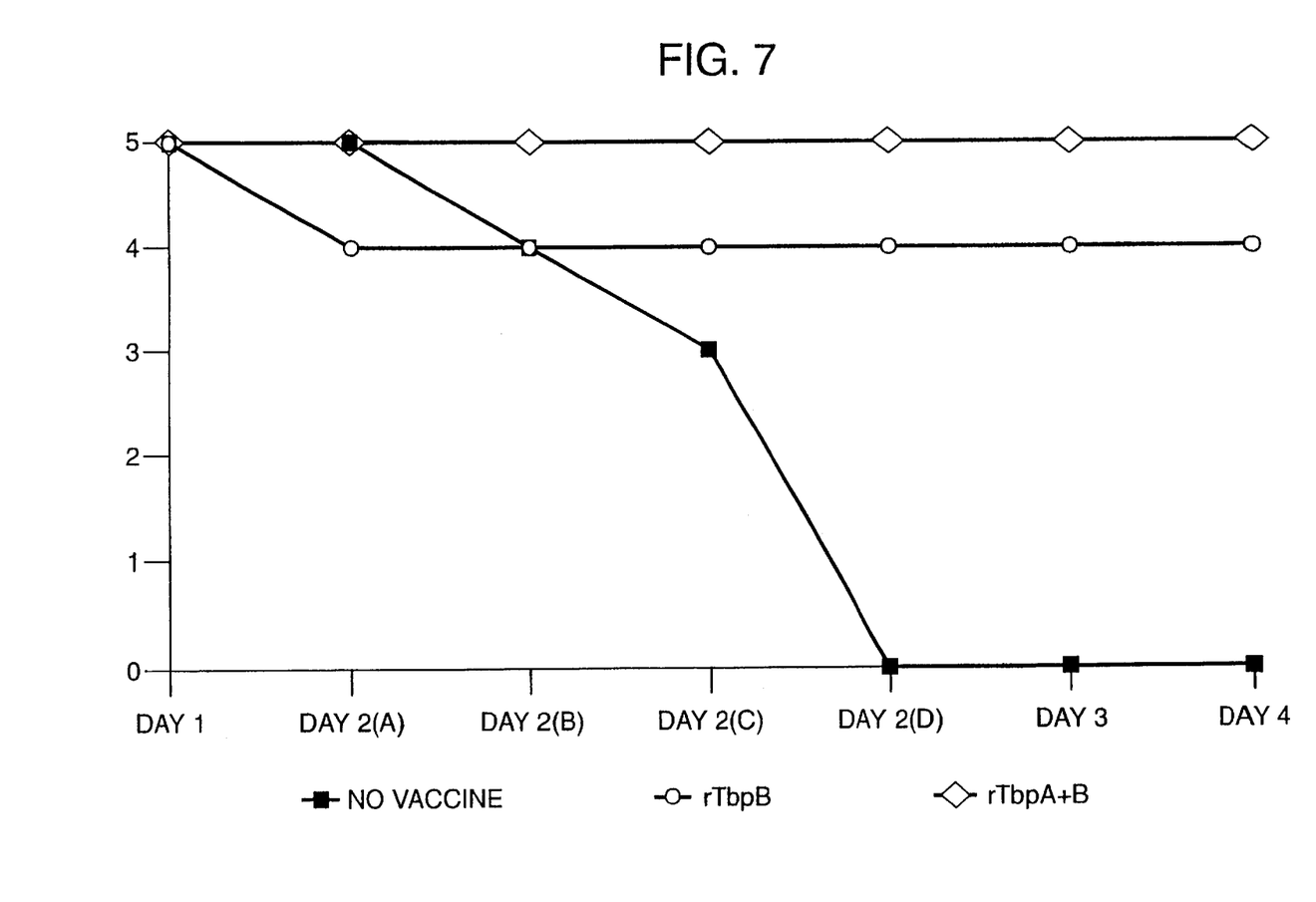

Interestingly, the results shown in FIGS. 4B and 5A–B, although arising from experiments of similar design, show the surprising variability associated with vaccine compositions that depend solely upon either TbpA or TbpB alone. In FIG. 4B the recombinant TbpA composition displayed low levels of protection compared to TbpB or TbpA+B. However, in FIGS. 5A and 5B the recombinant TbpA vaccine composition that showed high levels of protection comparable to the TbpA+B complex and the TbpB alone composition demonstrated poor protection to infection. This latter result is completely contrary to the teaching of the prior art.

Human Immune Response to TbpA and TbpB in Convalescent Sera

We have undertaken a number of studies looking at the antibody response in humans to TbpA and TbpB following meningococcal disease. The general conclusions are that both TbpA and TbpB are expressed during meningococcal disease and that an immune response is raised against them. The response is functional (opsonic) and is more cross-reactive between different meningococcal strains than is the response induced by immunisation of animals with Tbps. The immune response to TbpA appears to be stronger and more cross-reactive than that to TbpB, confirming the importance of the vaccine potential of TbpA.

TbpA and TbpB Form a Transferrin Receptor

Our structural studies indicate that the transferrin receptor on the meningococcal surface consists of two TbpA molecules and one TbpB molecule that act together.

Effect of a Vaccine Containing A+B Tbps

We carried out further tests of the efficacy of recombinant TbpB versus recombinant TbpA+B containing vaccine formulations against challenge from *N. meningitidis* strains L91 705 and B16B6, the results of which are illustrated in FIGS. 6 and 7 respectively. In both cases some improved protection was conferred by A+B compared to B alone.

References

Ala'Aldeen J. (1996) Med. Microbiol vol 44, pp237–243.

Boulton et al. (1998) Biochem. J. vol.334, pp269–273.

Feirrerós et al. (1998) Rev. in Med. Microbiol. vol 9, No. 1., pp29–37.

Gorringe et al. (1996) 10th Pathogenic Neisseria Conference, poster 46 abstract.

Martin et al. (1997) J Exp Med, vol. 185 no. 7 pp1173–1181.

Nassif et al. (1991) J Bacteriol, vol.173 no. 7 pp2147–54.

What is claimed is:

1. A composition comprising a meningococcal transferrin binding protein (Tbp) and isolated *N. meningitidis* outer membrane vesicles, wherein said outer membrane vesicles are enriched with added Tbp.

2. The composition of claim 1, comprising a Tbp selected from the group consisting of TbpA; TbpB; and a mixture of TbpA+TbpB.

3. The composition of clam 1, wherein said outer membrane vesicles are enriched with Tbps from different strains of *N. meningitidis.*

4. The composition of claim 1, wherein said outer membrane vesicles are enriched with *N. meningitidis* proteins other than Tbp.

5. The composition of claim 1, wherein said outer membrane vesicles comprise a mixture of outer membrane vesicles from different stains of *N. meningitidis.*

6. A method of manufacture of a composition, comprising:

(a) extracting a meningococcal Tbp from an outer membrane of a bacteria, and preparing an aqueous solution of said Tbp;

(b) extracting outer membrane vesicles from a culture of *N. meningitidis*, and preparing an aqueous solution of said outer membrane vesicles;

(c) obtaining a pharmaceutically acceptable carrier; and (d) admixing the solution prepared in (a), the solution prepared in (b) and the carrier obtained in (c), thereby obtaining a composition comprising said outer membrane vesicles enriched with added Tbps.

7. A composition obtained according to the method of claim 6.

8. A composition comprising isolated *N. meningitidis* outer membrane vesicles and a transferrin binding protein (Tbp), wherein said outer membrane vesicles are enriched with said Tbp and said Tbp is from a source selected from the group consisting of *N gonorrheae; N. lactamica*, and *Moraxella catarrhalis.*

* * * * *